United States Patent
Felder et al.

(10) Patent No.: US 7,691,068 B2
(45) Date of Patent: Apr. 6, 2010

(54) SYSTEM AND METHOD FOR PASSIVE MONITORING OF BLOOD PRESSURE AND PULSE RATE

(75) Inventors: Robin A. Felder, Charlottesville, VA (US); Majd Alwan, Charlottesville, VA (US); Steven W. Kell, Keswick, VA (US); David C. Mack, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 233 days.

(21) Appl. No.: 10/549,946

(22) PCT Filed: Mar. 26, 2004

(86) PCT No.: PCT/US2004/009099

§ 371 (c)(1),
(2), (4) Date: Sep. 20, 2005

(87) PCT Pub. No.: WO2004/091378

PCT Pub. Date: Oct. 28, 2004

(65) Prior Publication Data

US 2006/0173363 A1      Aug. 3, 2006

Related U.S. Application Data

(60) Provisional application No. 60/460,236, filed on Apr. 3, 2003.

(51) Int. Cl.
*A61B 5/02* (2006.01)

(52) U.S. Cl. ............... 600/500; 600/501; 600/502; 600/483; 600/485

(58) Field of Classification Search ............... 600/481, 600/483, 485, 486, 488, 508, 513, 527, 528, 600/490–504, 561
See application file for complete search history.

(56) References Cited

U.S. PATENT DOCUMENTS

| | | | | |
|---|---|---|---|---|
| 3,156,237 | A | * | 11/1964 | Edmark, Jr. .................. 600/496 |
| 4,299,233 | A | * | 11/1981 | Lemelson .................... 600/500 |
| 4,672,976 | A | * | 6/1987 | Kroll .......................... 600/528 |
| D297,364 | S | | 8/1988 | Slater |
| 4,880,013 | A | | 11/1989 | Chio |
| 4,909,339 | A | | 3/1990 | Burkhardt et al. |

(Continued)

FOREIGN PATENT DOCUMENTS

WO        WO 01/87143        11/2001

OTHER PUBLICATIONS

European Patent Office Communication with Supplementary European Search Report in the European Application No. EP 04758952 dated Apr. 24, 2009.

*Primary Examiner*—Charles A Marmor, II
*Assistant Examiner*—Navin Natnithithadha
(74) *Attorney, Agent, or Firm*—Robert J. Decker; Townsend and Townsend and Crew LLP

(57) ABSTRACT

System and method that can monitor pulse rate and passively produce a blood pressure measurement and automatically log the data for the user. Additionally, coupling to the Internet or Information Systems expands the options for the early detection of diseases, based on sudden detected changes and trend analyses, and the successful treatment of these patients while reducing the high costs associated with invasive procedures and in-hospital care.

34 Claims, 7 Drawing Sheets

U.S. PATENT DOCUMENTS

| | | | |
|---|---|---|---|
| 4,947,859 A * | 8/1990 | Brewer et al. | 600/528 |
| 5,022,402 A * | 6/1991 | Schieberl et al. | 600/484 |
| 5,094,244 A * | 3/1992 | Callahan et al. | 600/490 |
| 5,162,991 A * | 11/1992 | Chio | 600/510 |
| 5,241,964 A | 9/1993 | McQuilkin | |
| 5,351,694 A * | 10/1994 | Davis et al. | 600/485 |
| 5,365,930 A * | 11/1994 | Takashima et al. | 600/485 |
| 5,396,895 A * | 3/1995 | Takashima et al. | 600/500 |
| 5,396,896 A * | 3/1995 | Tumey et al. | 600/503 |
| 5,406,952 A * | 4/1995 | Barnes et al. | 600/485 |
| 5,448,996 A * | 9/1995 | Bellin et al. | 600/574 |
| 5,509,423 A * | 4/1996 | Bryars | 600/503 |
| 5,620,003 A | 4/1997 | Sepponen | |
| 5,671,751 A * | 9/1997 | Tumey et al. | 600/493 |
| 5,692,513 A * | 12/1997 | Davis et al. | 600/485 |
| 5,865,755 A | 2/1999 | Golub | |
| 6,186,953 B1 | 2/2001 | Narimatsu | |
| 6,221,010 B1 | 4/2001 | Lucas | |
| 6,398,740 B1 | 6/2002 | Lavery et al. | |
| 6,415,033 B1 * | 7/2002 | Halleck et al. | 381/67 |
| 6,416,483 B1 * | 7/2002 | Halleck et al. | 600/561 |
| 6,425,862 B1 | 7/2002 | Brown | |
| 6,428,481 B1 | 8/2002 | Inukai et al. | |
| 6,463,187 B1 | 10/2002 | Baruch et al. | |
| 6,475,153 B1 * | 11/2002 | Khair et al. | 600/485 |
| 6,503,206 B1 | 1/2003 | Li et al. | |
| 6,524,239 B1 | 2/2003 | Reed et al. | |
| 6,575,916 B2 * | 6/2003 | Halleck et al. | 600/528 |
| 6,616,613 B1 * | 9/2003 | Goodman | 600/504 |
| 6,618,616 B2 | 9/2003 | Iijima | |
| 6,640,212 B1 | 10/2003 | Rosse | |
| 6,687,424 B1 | 2/2004 | Gerdt et al. | |
| 6,696,956 B1 | 2/2004 | Uchida et al. | |
| 6,706,002 B1 * | 3/2004 | Halleck et al. | 600/586 |
| 6,752,760 B2 | 6/2004 | Kouou | |
| 6,984,993 B2 * | 1/2006 | Ariav | 324/639 |
| 7,374,540 B2 * | 5/2008 | Schnall | 600/481 |
| 7,601,123 B2 * | 10/2009 | Tweed et al. | 600/490 |
| 2002/0022773 A1 | 2/2002 | Drinan et al. | |
| 2002/0082486 A1 | 6/2002 | Lavery et al. | |
| 2002/0111541 A1 | 8/2002 | Bibl et al. | |
| 2003/0036685 A1 | 2/2003 | Goodman | |
| 2003/0199771 A1 | 10/2003 | Baruch et al. | |
| 2004/0092832 A1 * | 5/2004 | Schnall et al. | 600/490 |
| 2004/0111034 A1 * | 6/2004 | Lin et al. | 600/485 |
| 2005/0027206 A1 * | 2/2005 | Ariav | 600/529 |
| 2005/0148885 A1 * | 7/2005 | Tweed et al. | 600/490 |

* cited by examiner

SYSTEM AND METHOD FOR PASSIVE MONITORING OF BLOOD PRESSURE AND PULSE RATE

RELATED APPLICATIONS

This application is a national stage filing of International Application No. PCT/US2004/009099 which claims benefit under 35 U.S.C. Section 119(e) of the earlier filing date of U.S. Provisional Application Serial. No. 60/460,236, filed on Apr. 3, 2003, entitled "System and Method for Bathroom Scale that Monitors Blood Pressure and Pulse Rate (the Roboscale),"of which the entire disclosures are hereby incorporated by reference herein.

BACKGROUND OF THE INVENTION

Hypertension is a major risk factor that contributes to more than 625,000 fatal heart attacks and strokes each year in this country alone. Left untreated, high blood pressure can also lead to kidney and heart failure. With nearly 76 million baby boomers now approaching mid-life and beyond the numbers will continue to rise. It is well known that high blood pressure increases the risk of heart disease and stroke, which are the first and third leading causes of death for Americans. Based on National Health and Nutrition Examination Survey III [NHANES III, 1988-91], Centers for Disease Control and Prevention/National Center for Health Statistics about 50 million Americans aged 60 and older have high blood pressure (or hypertension). In fact, one in five Americans (and one in four adults) has high blood pressure and 31.6 percent of hypertensives are undiagnosed. It has been demonstrated that early detection and intervention results in dramatic reductions in mortality and morbidity in hypertensive subjects.

The NIH describes congestive heart failure as the "new epidemic." Over 4.8 million individuals in the USA are diagnosed with congestive heart failure, with 400,000-700,000 new cases reported each year. Within the next 5 years, 20 million Americans will discover symptoms that are early warning signs for impending congestive heart failure including increased blood pressure. An estimated 10 million persons have diabetes in USA. Diabetes puts patients at a high blood pressure, heart disease, circulatory problems, and vision problems. In diabetics, blood pressure control can help reduce long-term complications. Thus, there are many groups that can benefit from the use of passive, on-demand blood pressure measurements.

Most doctors will diagnose a person with high blood pressure on the basis of two or more pressure readings taken from the brachial artery over several office visits. For patients with disparate readings, home monitoring is the method of choice and is now reimbursed by health maintenance organizations (HMOs). Home monitoring of blood pressure has certain advantages; it will avoid what is sometimes termed "whitecoat hypertension" or elevated pressures due to nervousness in a doctor's office, and home monitoring of blood pressure will provide more accurate temporal measurements. Blood pressure can be measured using a variety of methods including mercury sphygmomanometer (the current gold standard), electronic blood pressure monitors, and by calculating blood pressure from mathematical transformations of pulse waves. For continuous blood pressure measurements, an ambulatory blood pressure monitoring device is employed. This device is usually worn for 24 hours and can take blood pressure at pre-programmed intervals (usually every 30 minutes). An ambulatory blood pressure device must be worn on the arm throughout the entire diagnostic period, which can be an inconvenience. Conventional blood pressure monitors have other disadvantages in that they are bulky, may cause hazardous mercury spills, and may be difficult to use by elder adults or the cognitively impaired. Furthermore, there is low patient compliance with taking blood pressure measurements regularly at home, due to the aforementioned disadvantages and/or inconveniences.

The ability to measure blood pressure and other vital signs, such pulse rate; weight; and body mass index (BMI), and percent body fat during the time it takes for a typical morning weight check, and then automatically store the information in a database for continuous analysis could have a beneficial effect on the early detection of disease.

BRIEF SUMMARY OF INVENTION

The present invention uses sensors to passively measure the various forces resulting from human (or animal) physiology. For the purposes of this invention, we will describe its use in humans; however this invention is applicable to any animate or animate body which generates forces. Various blood pressure parameters (for example but not limited to pulse rate, pulse width, pulse amplitude, pulse waveform area, pulse pressure, systolic blood pressure, diastolic blood pressure) may be derived from the information received from the sensor data through waveform analysis. This data may be transferred into a database and stored for future use and health status analysis. An example of future use would be longitudinal analysis, pattern recognition for diagnostic and other purposes. Consistent use of the platform and method will create opportunities for early detection and management of cardiovascular, and other diseases, or other conditions such as salt sensitivity.

This device and method allows a user to monitor blood pressure on a day-to-day basis thus reducing compliance issues while creating a longitudinal history.

We have developed a unique passive device and method designed to work alone, or in conjunction with caregivers, hospitals, and payers whose goals are better care and reduced costs. The "platform" is a passive blood pressure monitoring device and method which could be housed in the form factors for example but not limited to a standard bathroom scale, chair, a bath mat or bed.

An aspect of an embodiment of the present invention provides a blood pressure and/or pulse rate system for deriving the blood pressure and pulse of a subject that is in communication with an interface member. The system comprising: a sensor module in communication with the interface member, the sensor module for detecting a pulse wave form and pulse rate; and a processor module that analyzes the pulse wave form and pulse rate signal for deriving variants of blood pressure.

An aspect of an embodiment of the present invention provides a method for deriving the blood pressure and/or pulse of a subject that is in communication with an interface member. The method comprising: detecting a pulse wave form and pulse rate; and analyzing the pulse wave form and pulse rate signal for deriving variants of blood pressure.

An aspect of an embodiment of the present invention provides a computer program product comprising computer usable medium having computer logic for enabling at lease one processor in a computer system to derive the blood pressure and/or pulse of a subject that is in communication with an interface member. The computer logic comprising: detecting a pulse wave form and pulse rate; and analyzing the pulse wave form and pulse rate signal for deriving variants of blood pressure.

These and other objects, along with advantages and features of the invention disclosed herein, will be made more apparent from the description, drawings, and claims that follow.

BRIEF SUMMARY OF THE DRAWINGS

The foregoing and other objects, features and advantages of the present invention, as well as the invention itself, will be more fully understood from the following description of potential embodiments, when read together with the accompanying drawings in which.

DETAILED DESCRIPTION OF THE INVENTION

Figure 1:
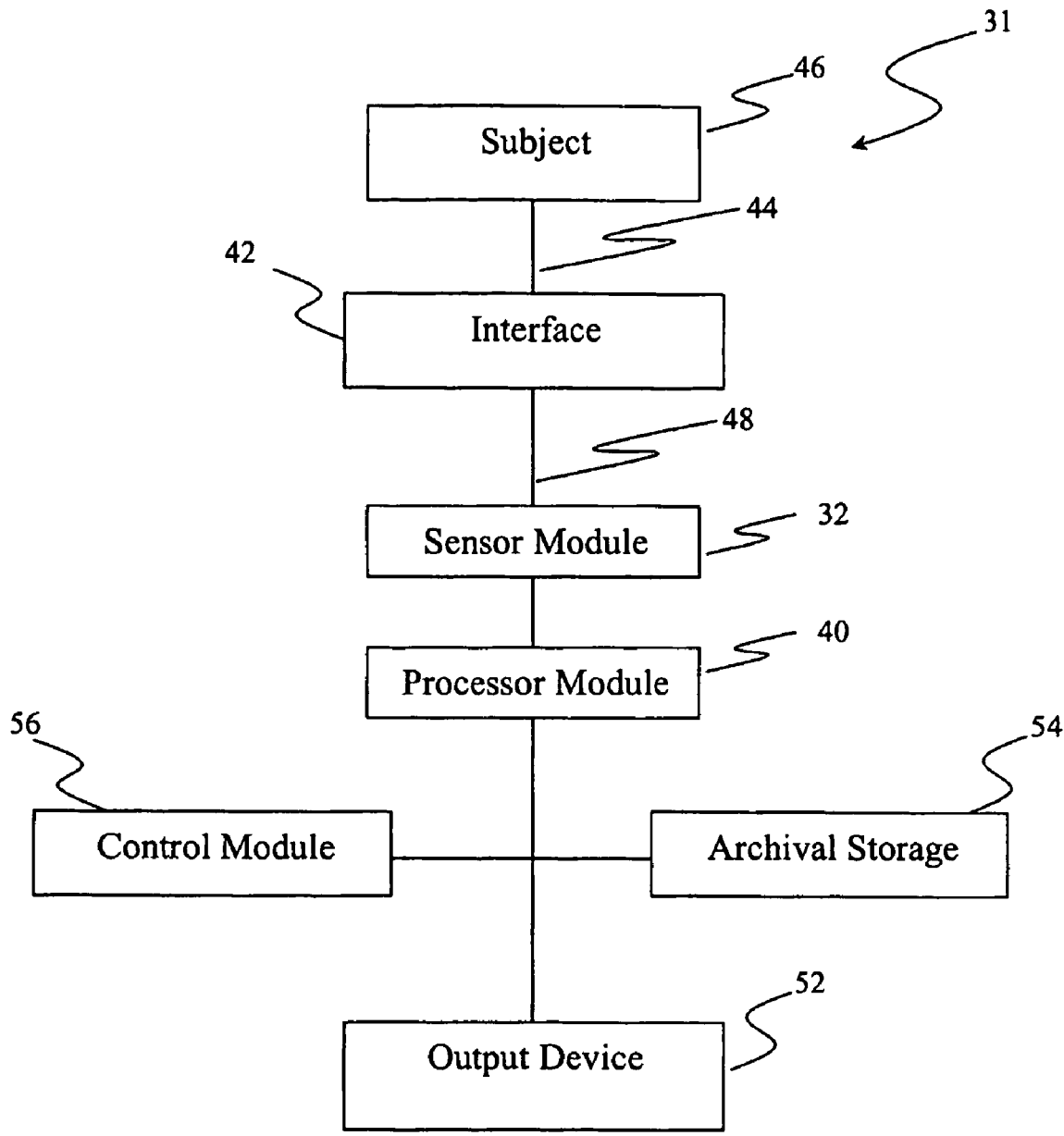
FIG. 1 is a schematic block diagram of the subject blood pressure and pulse rate system.

The present invention provides a new scale device (or other platform, interface, or structure) and methods that can monitor pulse rate and passively produce a blood pressure measurement and automatically log the data for the user. The present invention with an option for coupling to the Internet expands the options for the early detection of diseases, based on sudden detected changes and trend analyses, and the successful treatment of these patients while reducing the high costs associated with invasive procedures and in-hospital care.

Such a device would be of interest to a broad spectrum of health care professionals, payers and individual users. Some medical payers may include for example Independent Practice Associations (IPAs), Multispecialty Medical Groups, Subspecialty Medical Groups, Managed Care Organizations, Insurance Payers, Home Health Care Agencies, Disease State Management Companies, Hospital Systems, Congestive Heart Failure Clinics, Medicaid, and Medicare.

The present invention system and method are a platform that measures forces generated from the body in response to functioning human physiology. In the preferred use of the invention, a weighing scale is equipped with sensors that measure for example but not limited to respiration pulse and other physiological activity that emanate from subject. Alternatively, forces can be applied to the human body through the platform and measurements can be made of resultant physiological reactions. In one example embodiment, forces resulting from breathing and heart beat are measured as they emanate from the human foot or feet.

There are several types of sensor technologies that could be used to transduce the human forces into measurable signals in this invention. The sensors may be coupled to the human body directly or indirectly. For example a displacement or pressure sensor may translate movement resulting from physiological activity. A displacement sensor has the advantage of remaining operational at low frequencies of interest. The sensors can be coupled directly to the platform or any interface member with which the subject interacts (directly or indirectly). Alternatively, the energy emanating from the body may be transferred to the sensor element through a fluid, gas, or other medium. Any suitable sensor, processor, and data display technology can be incorporated into the design of the platform. In one embodiment, a highly sensitive transducer is used to monitor signals or movements that were transferred through closed system media contained in a pad or flexible bladder.

The invention relies on the unique construction of the platform that makes it possible to measure the forces emanating from the user, such as (but not limited to) those resulting from a subject's heartbeat, breathing, or other physiological activity. The platform with which the subject is in contact (for example but not limited to standing, sitting, laying, holding or touching) is designed to optimize the system performance, for example the signal to noise ratio sensitivity, specificity, et cetera.

Referring to FIG. 1, FIG. 1 provides a schematic block diagram of the present invention blood pressure and pulse rate system 31 for deriving the blood pressure and pulse of a subject or an object 46 that is in communication with an interface member 42. The system comprises a sensor module 32 in communication (directly or indirectly) with the interface member 42 that is used for detecting pulse wave form and pulse rate of the subject or object. The system further comprises a processor module 40 that analyzes the pulse wave form and pulse rate signal for deriving variants of blood pressure. The variants of blood pressure includes at least one of, but not limited thereto, pulse pressure, systolic pressure, diastolic pressure, pulse width, pulse time difference, double peak difference, and/or depth of dicrotic notch or the like. The system further comprises an output module for receiving said variants of blood pressure. The output module comprises at least one of, but not limited thereto, display, alarm, memory storage, communication device, printer, buzzer, PDA, lap top computer, computer, audio or visual alarm, and/or light or the like. It should be appreciated that the object or subject 46 is directly or indirectly coupled 44 to the interface member 42. Similarly, it should be appreciated that sensor module 32 is directly or indirectly coupled 48 to the interface member 42.

Still referring to FIG. 1, it should be appreciated that the system 31 or only portions of the system or communication paths of the system 31 (or with external devices) may be hardwired, wireless, or combination thereof. The sensor module 32 and processor module 40 are in wireless communication with one another along with other components of the system 31 as well as being in wireless communication with external devices or systems in communication with the system 31. Some examples of wireless communication include, but not limited thereto, at least one of RF link, BLUE TOOTH, an infrared, cellular phone link, optical and/or electromagnetic or the like. Alternatively, the sensor module 32 and processor module 40 are in a hard wired communication with one another along with other components of the system 31 as well as being in hardwired communication with external devices or systems in communication with the system 31. Some examples of hardwired communication include, but not limited thereto, electronic, integrated circuit, electromagnetic, wire, cable, fiber optics, a phone line, twisted pair, and/or coaxial, or the like.

Still referring to FIG. 1, an embodiment of the system may include at least one archival storage/memory 54. The archival storage/memory 54 stores at least one of longitudinal analysis of variants of blood pressure, pulse wave form, pulse rate and/or pattern recognition, or other data or diagnostics as required or desired for given application. Further, the processor module 40 or other secondary processors analyzes the longitudinal analysis of variants of blood pressure, pulse wave form, pulse rate and/or pattern recognition, or other data or diagnostics as required or desired for given application. In an embodiment the system further comprises a second processor module (not shown). The second processor module may be configured to analyze longitudinal analysis of variants of blood pressure, pulse wave form, pulse rate and/or pattern recognition, or other data or diagnostics as required or desired for given application. The subject or object 46 may be anyone of the following: human, animal, animate or inanimate object. The interface member 42 is at least one of scale, chair, bath mat, mat, bed, shoe, slipper, door knob, handle, and/or sandal or any suitable interface structure or communication. The sensor module 32 is at least one of but not limited to piezoelectric, fiber optic, differential transformer, and/or pressure of sufficient resolution to transduce the naturally occurring changes in physiology of the subject, which might be related to a cardiac event of interest (e.g. pulse). Such sensor may be directly or indirectly coupled to the subject. In an embodiment, the system 31 comprises a control module for controlling said sensor module and processor module.

Figure 2A:
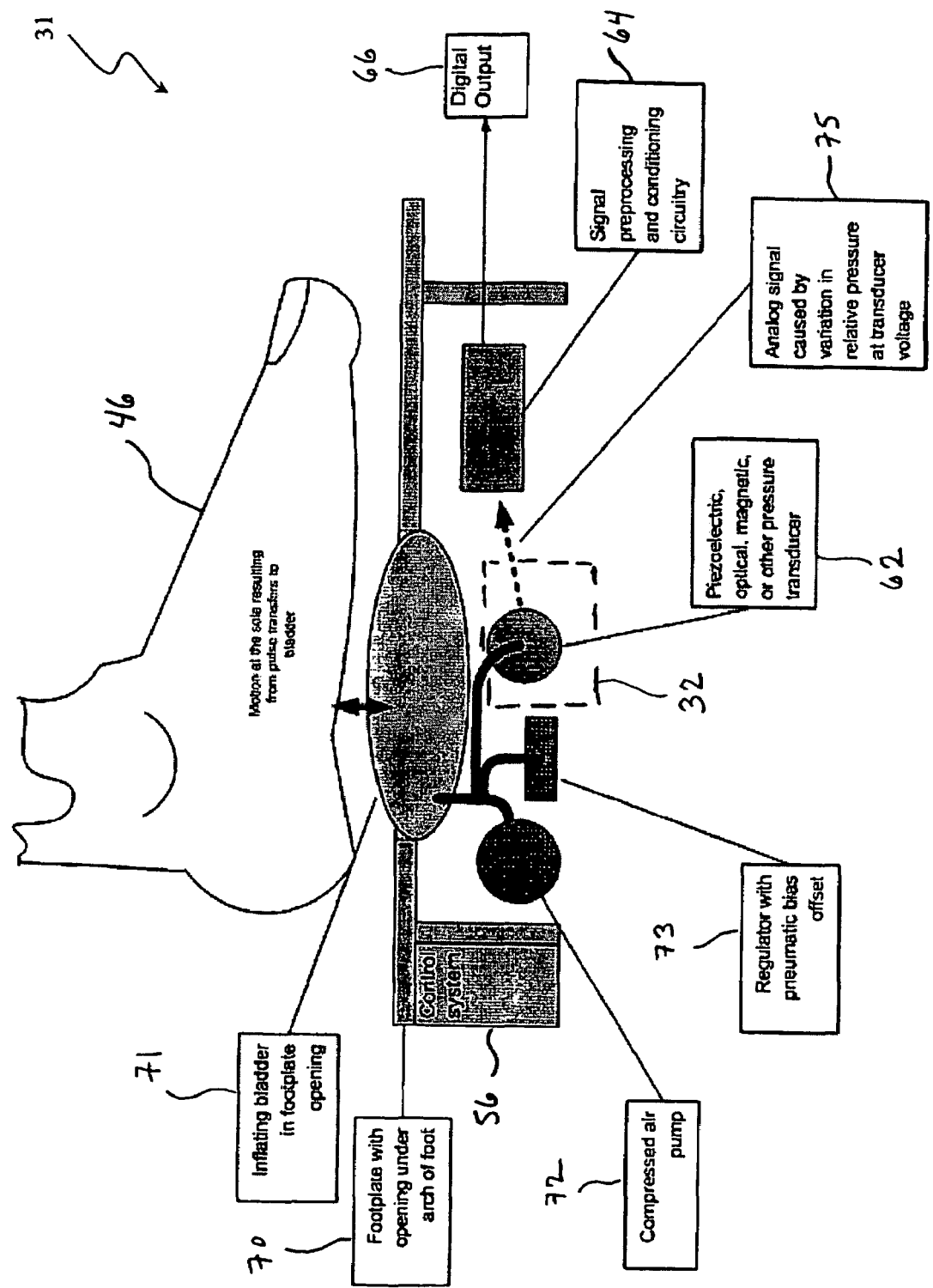
FIG. 2(A) provides a schematic illustration of a sensor system that can measure vibration using a pressure transducer in communication with an inflating bladder.

Referring to FIG. 2(A), FIG. 2(A) provides a schematic illustration of an exemplary embodiment of the present invention blood pressure and pulse system 31 having sensor system that can measure vibration using a piezoelectric, optical, magnetic, or other pressure transducer of a sensor module 32. During operation the foot 46 present to the plat 70 and the control system 56 initiates the deflation of the pre-pressurized bladder 71. The regulator 73 maintains the deflation process at a controlled rate. When the pulse wave in the pedal artery passes the bladder 71 (i.e., interface member) a compression of the enclosed volumes ensues. A sensor element (e.g., piezo pressure transducer or other type pressure transducer) is configured to respond to changes in pressure of the bladder volume. The resulting pulse wave indicates the pressure value at which occlusion occurs (systolic) and where the sensor no longer acquires the physiological effect (diastolic) of the pedal artery at the sole of the foot. Thus, the resultant signal is rich in information related to established pulse wave characteristics. This analog signal is preprocessed using selective filtering techniques and the pulse waveform derived is digitized for further analysis to derive the characteristics of interest such as pulse rate and pressure, etc.

In a similar aspect of an embodiment, a bladder presents to the arch area of the sole and inflates to a known pressure, greater than typical systolic pressure. The system includes a pressure transducer coupled to this bladder that translates the composite static/pulse pressure wave at the sole into an analog signal voltage. While continually sampling the analog signal and simultaneously deflating the bladder in a controlled manner, it is possible to derive the systolic pressure, the pulse wave shape, and thereby known characteristics of the pulse wave including but not limited to, for example, rate of pressure wave rise, dicrotic notch, pulse width, pulse time off, double peak spacing, slope of decrease, area(s) under the curve and so on. These metrics generate a rich set of pulse related data useful in calculating results of interest, including a blood pressure measure similar to yet distinct from established sphyganometer cuff methodology.

Figure 2B:
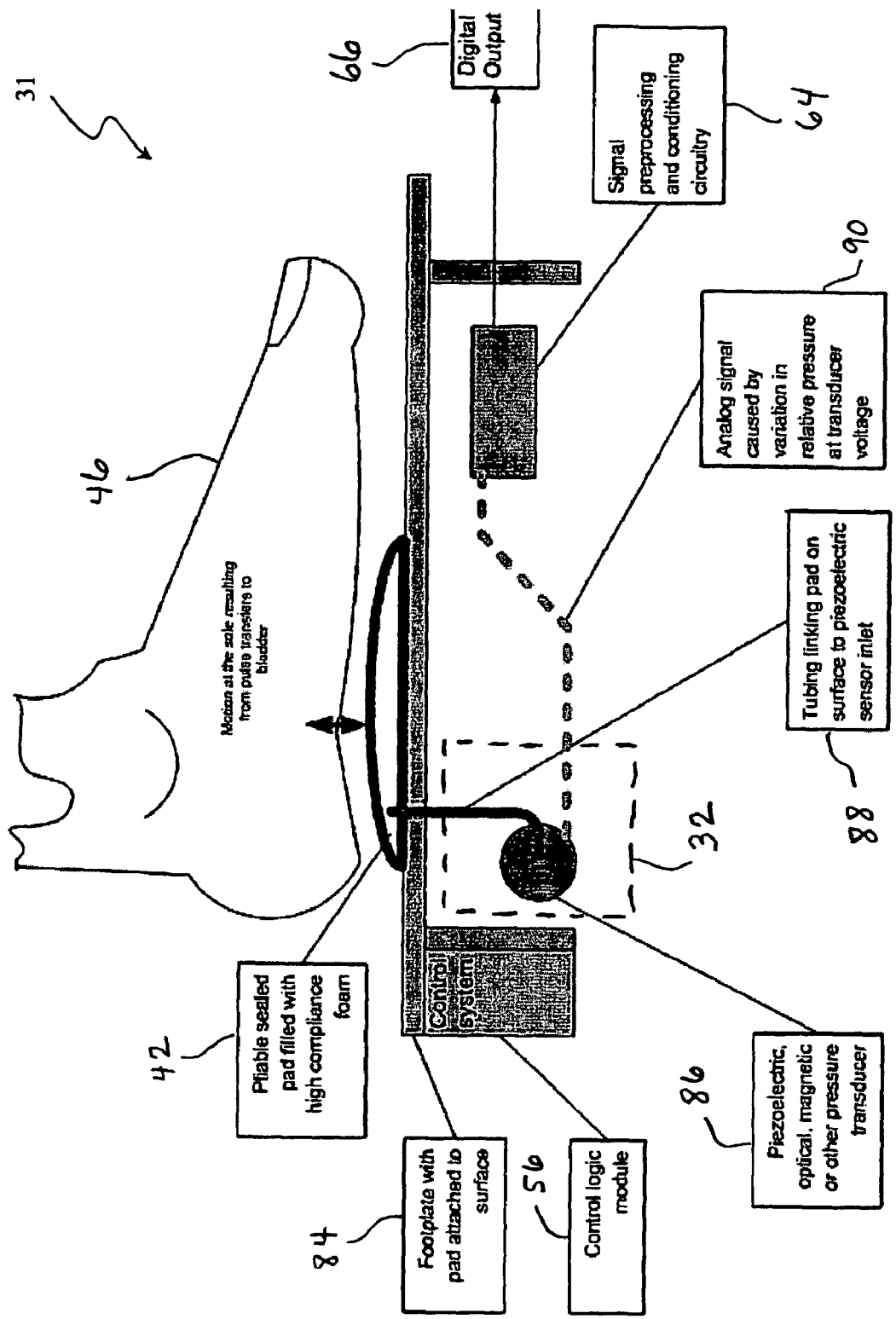
FIG. 2(B) provides a schematic illustration of a sensor system that can measure vibration using a pressure transducer in communication with a pad.

Referring to FIG. 2(B), FIG. 2(B) provides a schematic illustration of an exemplary embodiment of the present invention blood pressure and pulse system 31 having sensor system that can measure vibration using a piezoelectric sensor or crystal 86 (or other optical, magnetic or other transducer) of a sensor module 32. During operation the foot 46 presents to the plate 84 and the control system/module 56 initiates the acquisition of the signal. When the pulse wave passes the sealed pad 42 (i.e. interface member) a compression of the enclosed volume ensues. A piezoelectric pressure transducer inlet is coupled to the sealed pad 42 through a pressure conduit 88. The compression of the sealed pad 42 applies pressure to a piezoelectric device/material 86, which in turn has a shift in characteristics due to the pressure deformation. This change in characteristics is used to create an analog signal voltage 90. This analog signal is preprocessed 64 using selective filtering techniques and the pulse waveform derived is digitized for further analysis to derive the characteristics of interest such as pulse rate and pressure.

Herein provided are illustrative embodiments to demonstrate specific examples of the present invention method and system, or components of the system. These exemplary embodiments of the system or of the individual components should be considered illustrative only rather than restrictive.

EXAMPLE NO. 1

For example, (but not limited to), mantles can be constructed to contain the foot either loosely or under applied pressure. In iteration, the platform is designed to create openings on top of the scale, which calls for the subject to insert the front section of their feet into the opening, similar to stepping into a pair of slippers. Using the sensor, the foot sets off a trigger that causes a membrane to quickly inflate and cover the top of the foot creating a measure of force against the dorsalis pedis arteries. As the inflated membrane fills with air it is coupled via an air tube to a smaller inflated membrane bubble, creating a dynamic airflow system. It is over the smaller bubble that the sensor (fiber optic for example) is mounted and measures the change in the amount of pressure applied to the larger membrane, translating those changes by causing displacement in the volume of air within the system, working similar to a hydraulic system. The membranes will inflate until the sensor begins to receive a change in signal, which causes the inflation of the membranes to stop. The system is calibrated as such to create the best coupling between the membrane and subject foot artery. A clear measurement of the subjects pulse rate is then monitored, logged and stored for further waveform analysis. It is also possible to create a small opening in the floor of the scale where the foot is placed to allow for a membrane to inflate upward to the bottom of the foot to measure the pulse rate at the plantar artery.

EXAMPLE NO. 2

Figure 3A:
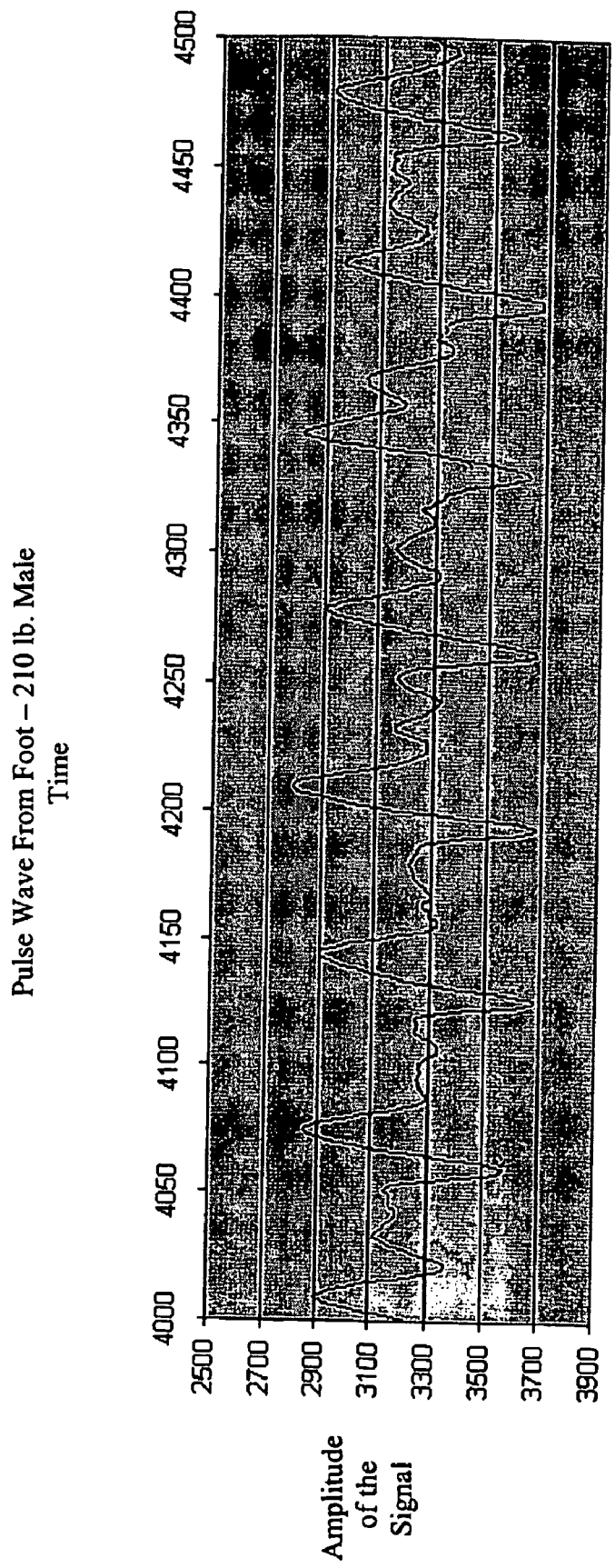
FIGS. 3(A)-(C) provide graphical representation of actual waveforms from an embodiment similar to the system depicted in FIG. 2B. The waveforms as depicted in FIGS. 3(A)-(C) provide respective portions of the minute sample taken.
Figure 3B:
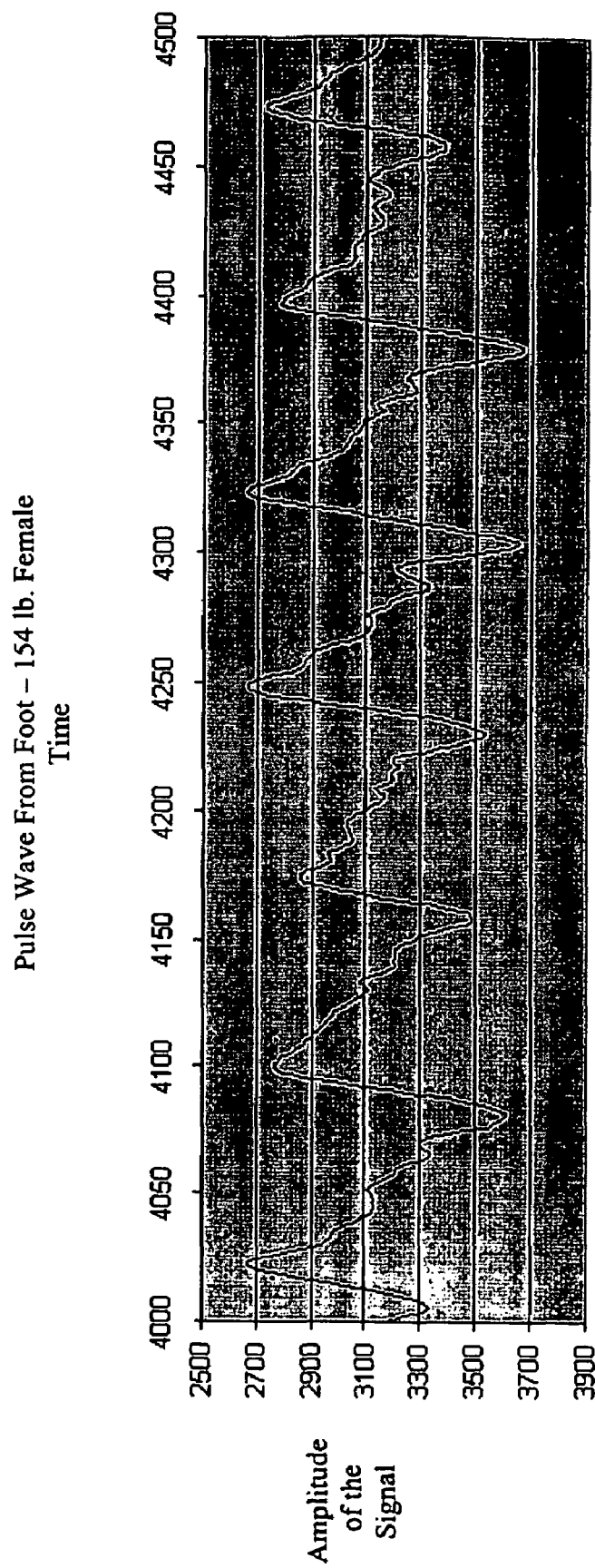
Figure 3C:
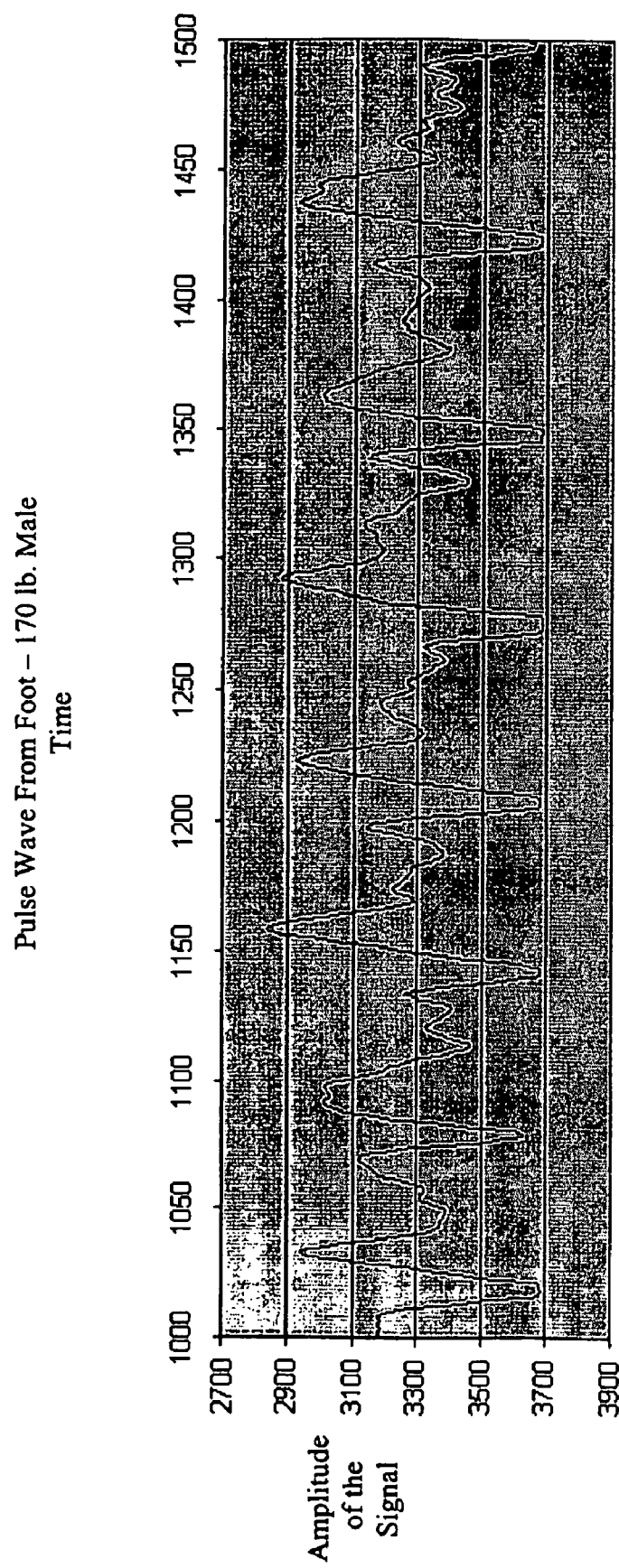

Turning to FIGS. 3(A)-(C), FIGS. 3(A)-(C) provide graphical representation of actual waveforms from an embodiment similar to the system depicted in FIG. 2B. The waveforms as depicted in FIGS. 3(A)-(C) provide respective portions of the minute sample taken. These waveforms are similar to the clinically acquired pedal pulse pressure waveforms. Information such as pulse rate and pulse pressure can be obtained from these waveforms.

Figure 3D:
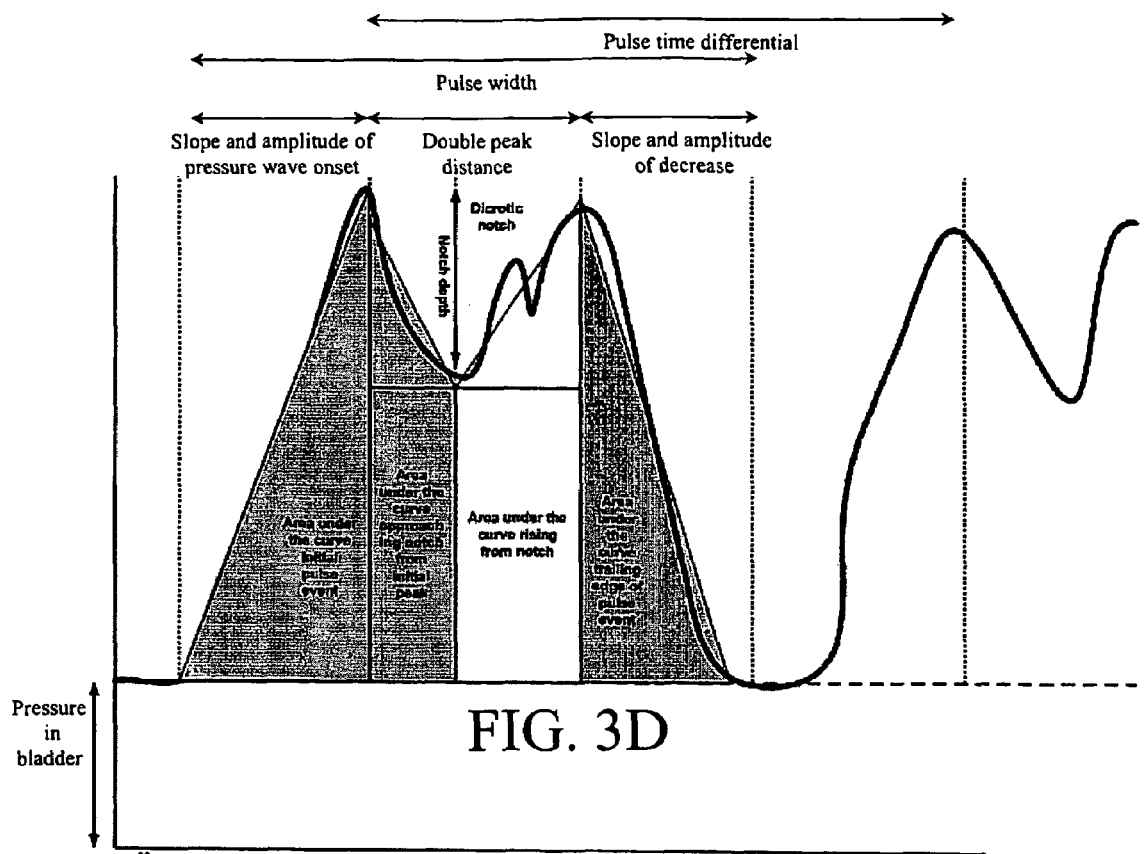
FIG. 3(D) provides graphical representation of a single heartbeat (i.e. one of the 7 peaks from FIG. 3(C)) which illustrates various characteristics that would be used in determining physiological parameters such as blood pressure, pulse wave velocity and pulse rate among others.

Turning to FIG. 3(D), FIG. 3(D) provides graphical representation of a single heartbeat (i.e. one of the 7 peaks from FIG. 3(C)) which illustrates various characteristics that would be used in determining physiological parameters such as blood pressure, pulse wave velocity and pulse rate among others.

Figure 3E:
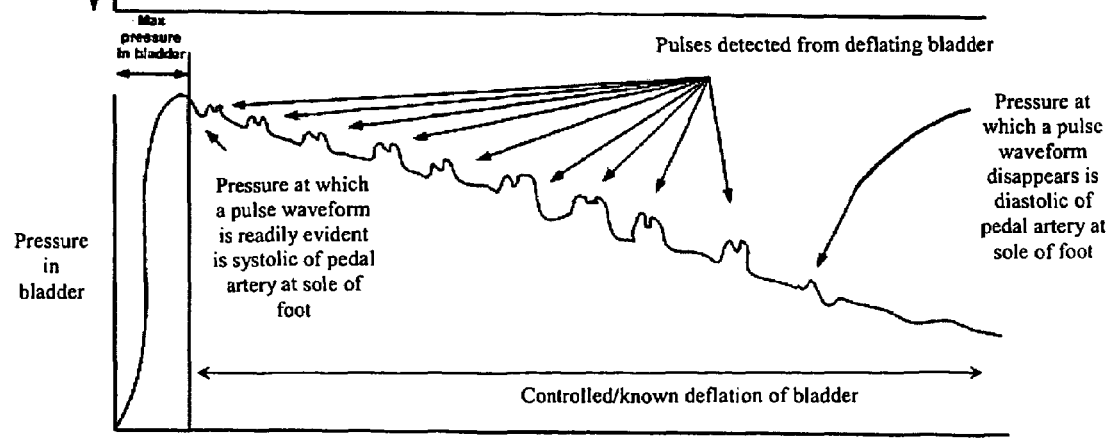
FIG. 3(E) provides graphical representation of a model used for determining blood pressure that is based on current clinical applications such as a sphygmomanometer.

Turning to FIG. 3(E), FIG. 3(E) provides graphical representation of a model used for determining blood pressure that is based on current clinical applications such as a sphygmomanometer. Thus, in this technique, the pad would be pre-inflated to occlude the pedal artery when the subject steps on the scale. Once the subject became quiescent, the pad would slowly deflate as depicted in FIG. 3(E).

EXAMPLE NO. 3

Data Interpretation

Once the pulse and breathing forces generated by the subject are recorded by an electronic device, breathing and pulse information can be derived from mathematical treatment of the data. Deriving blood pressure information from pulse data has been demonstrated by:

The Gary L. McQuilkin, U.S. Pat. No. 5,241,964, issued Sep. 7, 1993, assignee: Medwave, Inc. "Noninvasive, non-occlusive method and apparatus which provides a continuous indication of arterial pressure and a beat-by-beat characterization of the arterial system," of which is hereby incorporated by reference herein in its entirety.

Data Interpretation and Reporting

Data Interpretation and reporting can be demonstrated, for example, by Medical Advisory Systems, a global leader in telemedicine that has operated a 24/7, physician-staffed call center in Owings, Md.

Next, the method of present invention may be implemented using hardware, software or a combination thereof and may be implemented in one (or part of) or more computer systems or other processing systems, such as personal digit assistants (PDAs) or in communication with the same.

In an example embodiment, the invention was implemented in software running on a general purpose computer or the like. Computer system includes one or more processors. Such processor may be connected to a communication infrastructure (e.g., a communications bus, cross-over bar, or network). The computer system may include a display interface that forwards graphics, text, and other data from the communication infrastructure (or from a frame buffer not shown) for display on the display unit.

The Computer system may also include a main memory, preferably random access memory (RAM), and may also include a secondary memory. The secondary memory may include, for example, a hard disk drive and/or a removable storage drive, representing a floppy disk drive, a magnetic tape drive, an optical disk drive, a flash memory etc. The removable storage drive reads from and/or writes to a removable storage unit in a well known manner. Removable storage unit, represents a floppy disk, magnetic tape, optical disk, etc. which is read by and written to by removable storage drive. As will be appreciated, the removable storage unit includes a computer usable storage medium having stored therein computer software and/or data.

In alternative embodiments, secondary memory may include other means for allowing computer programs or other instructions to be loaded into computer system. Such means may include, for example, a removable storage unit and an interface. Examples of such removable storage units/interfaces include a program cartridge and cartridge interface (such as that found in video game devices), a removable memory chip (such as a ROM, PROM, EPROM or EEPROM) and associated socket, and other removable storage units and interfaces which allow software and data to be transferred from the removable storage unit to computer system.

The computer system may also include a communications interface. Communications interface allows software and data to be transferred between computer system and external devices. Examples of communications interface may include a modem, a network interface (such as an Ethernet card), a serial or parallel communications port, a PCMCIA slot and card, a modem etc. Software and data transferred via communications interface are in the form of signals, which may be electronic, electromagnetic, optical or other signals capable of being received by communications interface. Signals are provided to communications interface 124 via a communications path (i.e., channel). A channel (or any other communication means or channel disclosed herein) carries signals and may be implemented using wire or cable, fiber optics, a phone line, a cellular phone link, an RF link, an infrared link and other communications channels.

In this document, the terms "computer program medium" and "computer usable medium" are used to generally refer to media such as removable storage drive, a hard disk installed in hard disk drive, and signals. These computer program products are means for providing software to computer system. The invention includes such computer program products.

Computer programs (also called computer control logic) are stored in main memory and/or secondary memory. Computer programs may also be received via communications interface. Such computer programs, when executed, enable computer system to perform the features of the present invention as discussed herein. In particular, the computer programs, when executed, enable processor to perform the functions of the present invention. Accordingly, such computer programs represent controllers of computer system.

In an embodiment where the invention is implemented using software, the software may be stored in a computer program product and loaded into computer system using removable storage drive, hard drive or communications interface. The control logic (software), when executed by the processor, causes the processor to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in various programs and programming language known to those skilled in the art.

The following publications and patents are hereby incorporated by reference herein in their entirety:

U.S. Pat. No. 6,428,481 B1 to Inukai et al., entitled "Blood Pressure Monitor Apparatus;"

U.S. Pat. No. 6,425,862 B1 to Brown, entitled "Interactive Furniture for Dieters;"

U.S. Pat. No. 6,398,740 B1 to Lavery et al., entitled "Apparatus and Method for Monitoring the Temperatures on the Plantar Aspects of a Human Foot and Other Vital Health Information;"

U.S. Pat. No. 6,186,953 B1 to Narimatsu, entitled "Non-Invasive and Continuous Blood-Pressure Estimation Apparatus;"

U.S. Pat. No. 5,865,755 to Golub, entitled "Method and Apparatus for Non-Invasive, Cuffless, Continuous Blood Pressure Determination;"

U.S. Pat. No. 5,620,003 to Sepponen, entitled "Method and Apparatus for Measuring Quantities Relating to a Persons Cardiac Activity;"

U.S. Pat. No. 5,241,964 to McQuilkin, entitled "Noninvasive, Non-Occlusive Method and Apparatus Which Provides a Continuous Indication of Arterial Pressure and a Beat-by-Beat Characterization of the Arterial System;"

U.S. Pat. No. 4,909,339 to Burkhardt et al., entitled "Weight and Pressure Measuring Device;"

U.S. Pat. No. 4,880,013 to Chio, entitled "Method and Apparatus for Determining Blood Pressure and Cardiovascular Condition;"

U.S. Pat. Des. 297,364 to Slater, entitled "Console for Self-Measuring One's Weight, Height, Blood Pressure and Pulse Rate;"

U.S. Patent Application Publication 2002/0111541 A1 to Bibl et al., entitled "Personal Data Capture Device and Web Posting System;"

U.S. Patent Application Publication 2002/0082486 A1 to Lavery et al., entitled "Foot Temperature and Health Monitoring System;"

U.S. Patent Application Publication 2002/0022773 A1 to Drinan et al., entitled "Body Attribute Analyzer With Trend Display;"

U.S. Pat. No. 6,696,956 B1 to Uchida et al., entitled "Emergency Dispatching System;"

U.S. Pat. No. 6,687,424 B1 to Gerdt et al., entitled "Sensing Pad Assembly Employing Variable Coupler Fiberoptic Sensor;"

U.S. Pat. No. 6,640,212 B1 to Rosse, entitled "Standardized Information Management System for Long-Term Residence Facilities;"

U.S. Pat. No. 6,524,239 B1 to Reed et al., entitled "Apparatus for Non-Intrusively Measuring Health Parameters of a Subject and Method of Use Thereof;"

U.S. Pat. No. 6,463,187 B1 to Baruch et al., entitled "Variable Coupler Fiberoptic Sensor and Sensing Apparatus Using the Sensor;"

U.S. Pat. No. 6,221,010 B1 to Lucas, entitled "Home Medical Supervision and Monitoring System;"

U.S. Pat. No. 6,221,010 B1 (Certificate of Correction) to Lucas, entitled "Home Medical Supervision and Monitoring System;" and U.S. Patent Application Publication 2003/0199771 A1 to Baruch et al., entitled "Apparatus and Method for Measuring Pulse Transit Time."

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. A blood pressure and pulse rate system for deriving the blood pressure and pulse of a subject, said system comprising:
   a platform configured to accommodate a foot of the subject;
   an interface member configured:
      to be presented to the foot of the subject,
      to be maintained at a substantially constant pressure, and
      to function when in indirect contact with the subject's body;
   a sensor module in communication with said interface member, said sensor module configured to detect a pulse wave form from the foot of the subject and a pulse rate of the subject when the foot of the subject is presented to the interface member and the interface member is maintained at the substantially constant pressure;
   a processor module configured to analyze the pulse wave form and pulse rate signal and to derive a pulse pressure of the subject based on the analysis; and
   an output module configured to output at least one of the pulse wave form, pulse rate and pulse pressure.

2. The system of claim 1, wherein said processor module is further configured to derive pulse width, a pulse time difference, a double peak difference, and a depth of dicrotic notch for the subject based on the analysis.

3. The system of claim 1 wherein said output module comprises at least one of display, alarm, memory storage, communication device, printer, buzzer, PDA, lap top computer, computer, audio and visual alarm, and light.

4. The system of claim 1, wherein said interface member is also configured to function when in direct contact with the subject's body.

5. The system of claim 1, wherein said sensor module is indirectly coupled to the interface member.

6. The system of claim 1, wherein said sensor module and processor module are configured for wireless communication.

7. The system of claim 6, wherein said wireless communication comprises at least one of RF link, infrared link, cellular phone link, optical link and electromagnetic link.

8. The system of claim 1, wherein said sensor module and processor module are configured for hard wired communication.

9. The system of claim 8, wherein said hard wired communication comprises at least one of electronic, integrated circuit, electromagnetic, wire, cable, fiber optics, a phone line, twisted pair, and coaxial.

10. The system of claim 1, further comprising an archival storage module.

11. The system of claim 10, wherein said archival storage module is configured to store at least one of longitudinal analysis and pattern recognition.

12. The system of claim 11, wherein said processor module performs at least one of longitudinal analysis and pattern recognition analysis.

13. The system of claim 11, further comprising: a second processor module, said second processor module configured to analyze the longitudinal analysis, and pattern recognition.

14. The system of claim 1, wherein said interface member is included in at least one of a scale, a bath mat, a shoe, a slipper, and a sandal.

15. The system of claim 1, wherein said sensor module comprises at least one of piezoelectric device, fiber optic device, differential transformer, and pressure determining device providing sufficient resolution to transduce the naturally occurring changes in physiology related to the subject of interest cardiac event.

16. The system of claim 15, wherein said sensor module is indirectly coupled to the subject.

17. The system of claim 1, farther comprising a control module for controlling said sensor module and processor module.

18. The system of claim 1, wherein said sensor module is indirectly coupled to the subject.

19. The system of claim 1, wherein said interface member is included in a scale, and the system is configured to detect the pulse wave form when the subject stands on the scale.

20. The system of claim 1, wherein said interface member is included in at least one of a shoe, a slipper, and a sandal, and the system is configured to detect the pulse wave form when the subject wears the at least one of a shoe, a slipper, and a sandal.

21. A method for deriving the blood pressure and pulse of a subject, said method comprising:
   detecting a pulse wave form and pulse rate from a foot of the subject via an interface member, the foot of the subject presented to the interface member;
   analyzing, by a processor module, the pulse wave form and pulse rate signal and deriving a pulse pressure of the subject based on the analysis; and
   outputting, by an output module, at least one of the pulse wave form, the pulse rate and the pulse pressure,
   wherein the interface member is inflated and maintained at a substantially constant pressure and is configured to function when in indirect contact with the subject's body.

22. The method of claim 21, further comprising deriving a pulse width, a pulse time difference, a double peak difference, and a depth of dicrotic notch for the subject based on the analysis.

23. The method of claim 21, wherein said outputting is provided by an output module.

24. The method of claim 23, wherein said output module comprises at least one of display, alarm, memory storage, communication device, printer, buzzer, PDA, lap top computer, computer, audio or visual alarm, and light.

25. The method of claim 21, further comprising: storing archival information based on the pulse wave form, the pulse rate and the pulse pressure.

26. The method of claim 25, wherein the storing of archival information is provided by an archival storage module that stores at least one of longitudinal analysis and pattern recognition.

27. The method of claim 25, further comprising:
   performing at least one of longitudinal analysis and pattern recognition analysis based on the archival information.

28. The method of claim 21, wherein the interface member is also configured to function when in direct contact with the subject's body.

29. The method of claim 21, wherein said interface member is included in at least one of a scale, a bath mat, a shoe, a slipper, and a sandal.

30. The method of claim 21, wherein said interface member is included in a scale, and the detecting is performed while the subject stands on the scale.

31. A computer program product comprising computer usable medium having computer logic for enabling at lease one processor in a computer system to derive the blood pressure and pulse of a subject, said computer logic comprising instructions for:
   detecting a pulse wave form and pulse rate from a foot of the subject via an interface member, the foot of the subject presented to the interface member;
   analyzing the pulse wave form and pulse rate signal and deriving a pulse pressure of the subject based on the analysis; and
   outputting at least one of the pulse wave form, the pulse rate and the pulse pressure,
   wherein the interface member is inflated and maintained at a substantially constant pressure and is configured to function when in indirect contact with the subject's body.

32. The product of claim 31, wherein the interface member is also configured to function when in direct contact with the subject's body.

33. The product of claim 31, wherein said interface member is included in at least one of a scale, a bath mat, a shoe, a slipper, and a sandal.

34. The product of claim 31, wherein said interface member is included in a scale, and the system is configured to detect the pulse wave form when the subject stands on the scale.

* * * * *